United States Patent [19]

Corcuff et al.

[11] Patent Number: 5,719,700
[45] Date of Patent: Feb. 17, 1998

[54] APPARATUS FOR IN VIVO OBSERVATION OF THE MICROSCOPIC STRUCTURE OF THE SKIN OR OF A SIMILAR TISSUE

[75] Inventors: Pierre Corcuff, Neuilly-Sur-Marne; Jean-Luc Leveque, Le Raincy, both of France

[73] Assignee: L'Oreal, Paris, France

[21] Appl. No.: 791,932

[22] Filed: Jan. 31, 1997

Related U.S. Application Data

[63] Continuation of Ser. No. 211,069, Mar. 18, 1994, abandoned.

[30] Foreign Application Priority Data

Oct. 11, 1991 [FR] France .................... 91 12541

[51] Int. Cl.$^6$ .................... G02B 21/00; G02B 5/08; G02B 26/08
[52] U.S. Cl. .................... 359/368; 359/351; 359/379; 359/380; 359/382; 359/383; 359/350; 359/223; 359/381
[58] Field of Search .................... 359/368, 351, 359/379, 380, 382, 383, 392, 506, 350, 656, 223, 369, 381, 821

[56] References Cited

U.S. PATENT DOCUMENTS

| | | | |
|---|---|---|---|
| 3,809,454 | 5/1974 | Brambring | 359/382 |
| 3,820,879 | 6/1974 | Frisen | 351/219 |
| 3,837,731 | 9/1974 | Amos et al. | 359/656 |
| 4,208,101 | 6/1980 | Trapp et al. | 359/656 |
| 4,465,621 | 8/1984 | Sacher | 252/582 |
| 4,491,533 | 1/1985 | Sacher et al. | 252/301.16 |
| 4,662,747 | 5/1987 | Isaacson et al. | 359/368 |
| 4,761,381 | 8/1988 | Blatt et al. | 436/165 |
| 4,789,490 | 12/1988 | Tanaka | 252/1 |
| 4,893,886 | 1/1990 | Ashkin et al. | 359/350 |
| 4,912,388 | 3/1990 | Tanaka et al. | 318/640 |
| 4,913,545 | 4/1990 | Volk | 351/219 |
| 4,988,158 | 1/1991 | Yamamoto | 350/96.18 |
| 5,000,548 | 3/1991 | Mercado | 359/656 |
| 5,004,307 | 4/1991 | Kino et al. | 359/368 |
| 5,032,020 | 7/1991 | Robert | 351/219 |
| 5,184,021 | 2/1993 | Smith | 250/560 |
| 5,283,684 | 2/1994 | Thomas et al. | 359/234 |
| 5,307,203 | 4/1994 | Hill | 359/368 |
| 5,337,177 | 8/1994 | Toyoda et al. | 359/368 |

FOREIGN PATENT DOCUMENTS

| | | | |
|---|---|---|---|
| 158318 | 12/1981 | Japan | 359/368 |
| 121417 | 6/1987 | Japan | 359/656 |

OTHER PUBLICATIONS

JOURNAL OF ELECTRON MICROSCOPY TECHNIQUE, vol. 18, 1991, pp. 50–60; Jester et al., "In Vivo, Real Time Confocal Imaging".

SCANNING, vol. 13, No. 5, Sep. 1991, pp. 369–372, New et al., "In Vivo Imaging of Human Teeth and Skin Using Real-Time Confocal Microscopy".

PATENT ABSTRACTS OF JAPAN, vol. 13, No. 12 (P-812) 12 Jan. 1989 & JP.A.63 218 911 (Hairotsukusu) 12 Sep. 1988.

EXPERIENTIA, vol. 24, 15 Nov. 1968, BASEL CH, pp. 1094–1095, Maurice "Cellular Membrane Activity in the Corneal Endothelium of the Intact Eye".

JOURNAL OF MICROSCOPY, vol. 170, Pt. 3, Jun. 1993, pp. 213–219, Petroll et al., "Three Dimensional Imaging of Corneal Cells Using in vivo Confocal Microscopy".

SPECIFICATIONS FOR THE MODEL 165A OPHTHALMIC TANDEM SCANNING CONFOCAL MICROSCOPE AND OBJECTIVE LENS, Sep. 1, 1990.

PCT Search Report dated Jan. 23, 1993.

French Search Report dated for Jul. 14, 1992, for priority French Application Ser. No. 91/12541.

*Primary Examiner*—Paul M. Dzierzynski
*Assistant Examiner*—Mohammad Y. Sikder
*Attorney, Agent, or Firm*—Staas & Halsey

[57] ABSTRACT

A confocal microscope equipped with a light source, a rotary disk having holes, a highly sensitive image receiver or camera, an immersion lens, and a contact endpiece for contacting the skin and in which is engaged at least a lower part of the lens. The endpiece includes a central opening and abuts the skin about the central opening. The microscope allows for relative axial displacement of the contact end-piece relative to the lens.

8 Claims, 4 Drawing Sheets

APPARATUS FOR IN VIVO OBSERVATION OF THE MICROSCOPIC STRUCTURE OF THE SKIN OR OF A SIMILAR TISSUE This application is a continuation of application Ser. No. 08/211,069, filed as PCT/FR92/00924 Oct. 5, 1992, published as WO93/07522 Apr. 15, 1993, now abandoned.

BACKGROUND OF THE INVENTION

The invention relates to an apparatus for in vivo observation of the microscopic structure of the skin or of a similar tissue, over a sufficient depth from an external surface.

Ultrasonic apparatuses or apparatuses utilizing nuclear magnetic resonance (NMR) have already been proposed for observing, in situ, the human skin.

The spatial resolution is relatively limited, of the order of 100 microns, and is not sufficient for an observation on the cellular scale.

In other words, the apparatuses proposed to date for the in vivo observation of the skin do not make it possible to perform observations which are as fine and precise as those effected in vitro, by destructive or invasive means.

It has moreover been proposed to utilize confocal microscopy, in real time, to obtain images of cells of tissues in vivo, in particular for the cornea of the eye. The article "IN VIVO REAL-TIME CONFOCAL IMAGING" by JAMES V. JESTER, PETER M ANDREWS, W. MATTHEW PETROLL, MICHAEL A. LEMP and H. DWIGHT CAVANAGH published in May 1991 in "Journal of Electron Microscopy Technique", 18 (1991) pages 50–60, gives various examples in connection with the subject. However, in that publication there is no reference to any apparatus configuration permitting the formation of in vivo images of the skin, by confocal microscopy.

SUMMARY OF THE INVENTION

The object of the invention is, above all, to provide an apparatus for in vivo observation, in a non-invasive manner, of the microscopic structure of the skin or of a similar tissue, with a precision comparable to that obtained by the in vitro observation methods, which are destructive or invasive. It is desirable, moreover, that such an apparatus should permit rapid observations to be performed.

According to the invention, an apparatus for in vivo observation of the microscopic structure of the skin or of a similar tissue includes a confocal microscope equipped with an appropriate illumination, and with a rotary disk provided with reduced diameter holes, generally known under the name of a Nipkov disk, with a highly sensitive image receiver and with an immersion lens; it includes a contact endpiece intended to be placed against the skin and in which is engaged at least the lower part of said lens, this endpiece including a central opening and being linked to the skin about said central opening, the whole being mounted in such a manner that a relative axial displacement is possible between the contact endpiece and the lens.

For the observation, a drop of a liquid, the refractive index of which is substantially equal to that of the upper layer of the skin (stratum corneum) is placed in the central opening of the contact endpiece, between the lens and the skin, with which lens and skin said drop is in contact. The liquid is advantageously composed of an immersion oil, the refractive index of which is equal to 1.5.

The apparatus of the invention, while assuring the retention of the zone of the skin to be observed, and while facilitating the placing in position and the preservation of the drop of immersion liquid, permits quality images to be obtained. The invention has overcome a prejudice linked to the flexible and deformable nature of the skin, leading to the view that it was not feasible to utilize confocal microscopy for imaging of the skin.

Advantageously, the contact endpiece includes a channel, especially a capillary channel, permitting the resupply of liquid to said central opening of the contact endpiece.

The contact endpiece may be linked to the skin by means of a double-face adhesive washer including a central hole, in correspondence with the central opening of the contact endpiece.

Preferably, the contact endpiece is fixed in a detachable manner, especially by screwing, onto an arm.

According to a one embodiment, the lens of the confocal microscope is carried by a fixed support, while the contact endpiece is mounted for sliding relative to the lens.

According to another embodiment, the lens may be displaced manually, especially in order to reach different sites of the body, said lens moreover being mounted for being slidingly displaced relative to the contact endpiece, immovable on the skin.

Micrometric displacement means, especially actuated by a stepping electric motor, are advantageously provided to control the relative displacements between the lens and the contact endpiece. These means moreover permit precise measurements of the depths reached.

The confocal microscope is illuminated with white light, especially by a mercury lamp filtered within the band 400 nm–700 nm.

The highly sensitive image receiver advantageously includes a DAGE MTI SIT 68 intensified camera ($10^{-5}$ lux).

The lens has a magnification in the order of 50, and a numerical aperture (NA) generally exceeding 0.7 and preferably of 0.85.

The front distance of the lens is at least equal to 200 micrometers.

BRIEF DESCRIPTION OF THE DRAWINGS

The invention includes, apart from the arrangements set out hereinabove, in a certain number of other arrangements, more explicit details of which will be given hereinbelow, with reference to the accompanying drawings, in relation to an embodiment of an apparatus according to the invention, but which is in no sense limiting.

Finally.

DESCRIPTION OF THE PREFERRED EMBODIMENTS

Figure 1:
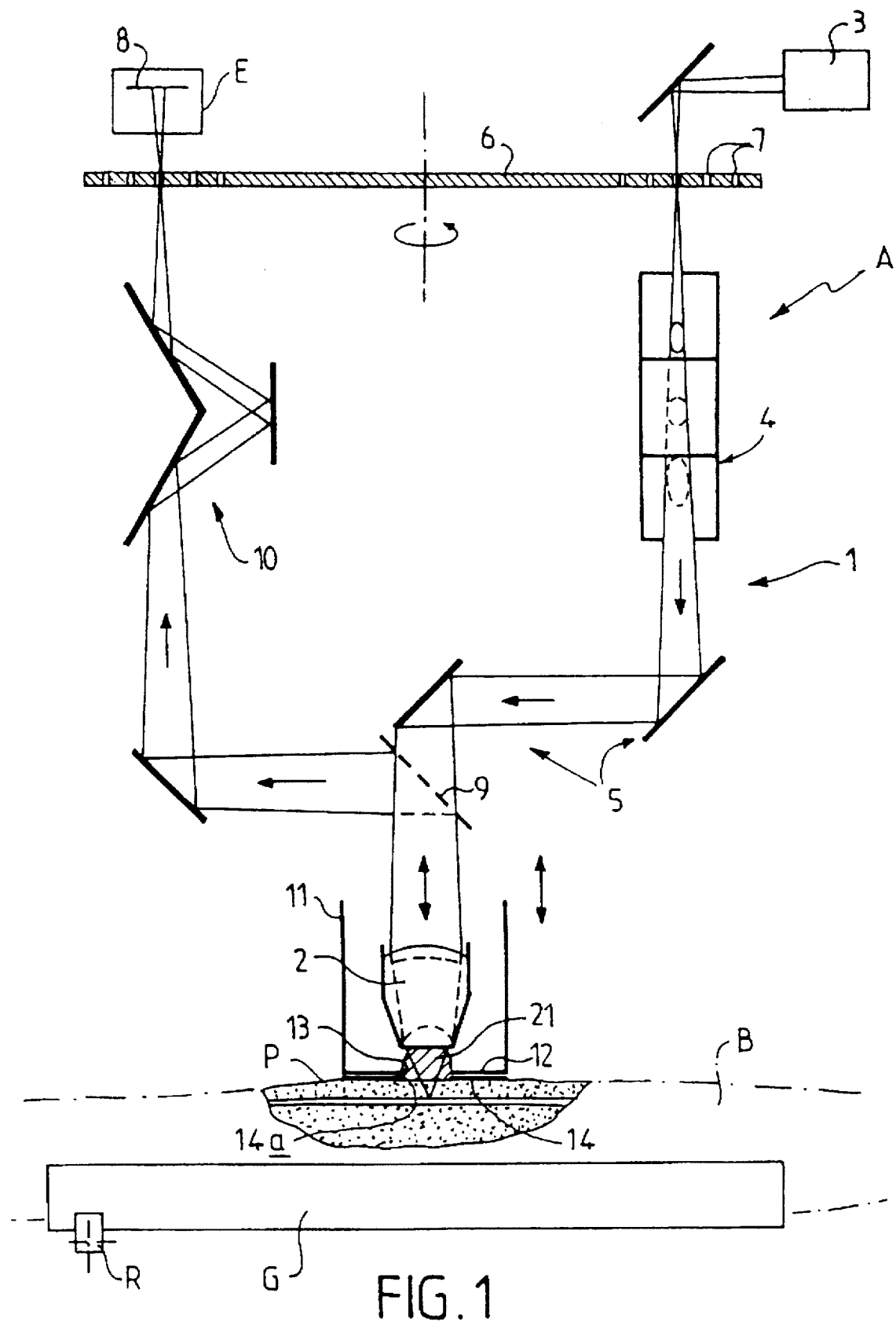
FIG. 1 of these drawings is a diagram of the apparatus according to the invention.

Referring to the drawings, especially to FIG. 1, it is possible to see an apparatus A permitting the in vivo observation of the microscopic structure of the skin. In the embodiment under consideration, the apparatus A is utilized for observing a zone of the skin P of the arm B of a patient.

The apparatus A includes a confocal microscope 1, for example of the TSM TRACOR type, for observation in real time. This microscope 1 is provided with an oil immersion lens 2, the magnification of which is advantageously equal to 50 and the numerical aperture of which is equal to 0.85. The front distance of the lens 2 (that is to say the distance between its exit face and the focus) is at least equal to 200 microns. The illumination of the zone to be observed is assured by a white light source 3, for example a mercury lamp, filtered within the band 400–700 nm. The light beam passes through an inverter system 4 and is reflected by a set of mirrors 5, or equivalent means, along the optical axis of the lens 2.

Figure 2:
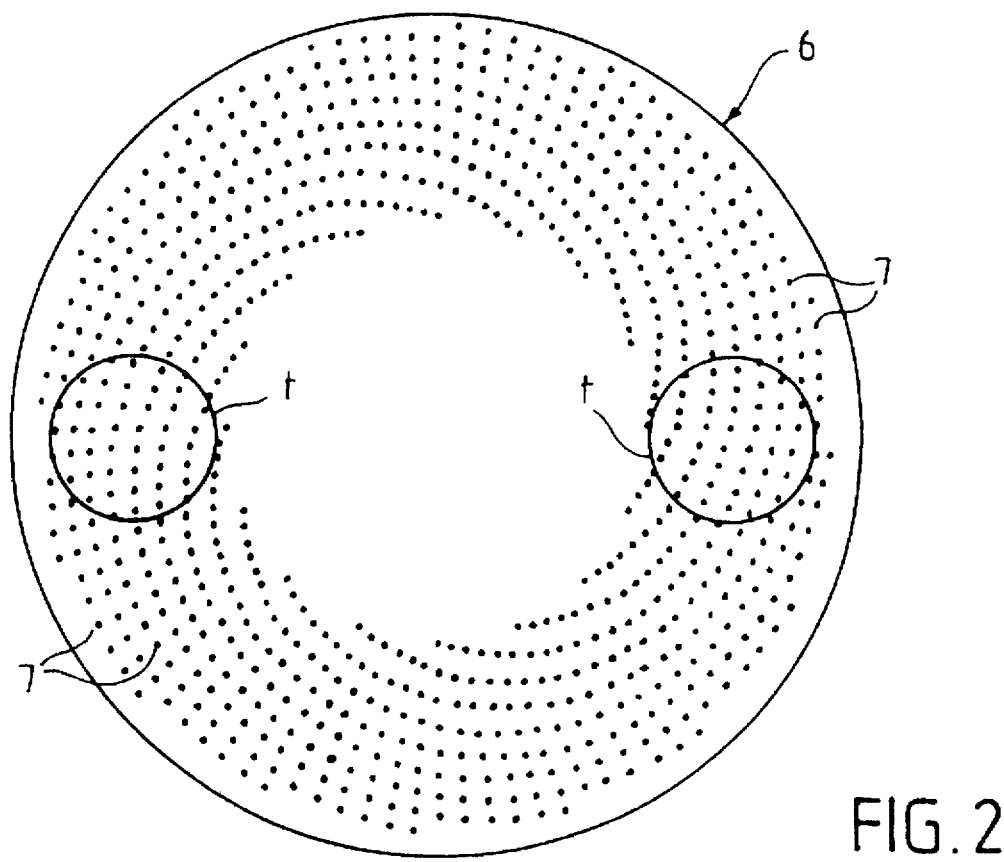
FIG. 2 is a plan view of the Nipkov disk of the confocal microscope of the apparatus of FIG. 1.

In a known manner, in order to assure the scanning of the zone to be observed, by a light spot focused by the lens 2, the light beam originating from the source 3 is chopped by a disk 6 including a multiplicity of reduced diameter holes 7 (see FIG. 2), which are judiciously distributed. The disk 6 is driven in rotation about an axis perpendicular to its plane and parallel to the axis of the chopped light beam.

The disk 6 is known under the name of a Nipkov disk.

The light reflected by the zone P to be observed is focused on a highly sensitive receiver surface 8, including a receiver surface of an intensified camera E, for example of the DAGE MTI SIT 68 type, which is sensitive down to $10^{-5}$ lux. The light reflected by the zone P to be observed is directed towards the sensitive surface 8 by a semi-transparent mirror 9, or equivalent, and by a set of reflecting surfaces 10. Before reaching the surface 8, the reflected beam passes through holes 7 of the disk 6.

Traces of the light beams on the disk 6 are diagrammatically represented by circles t.

Figure 3:
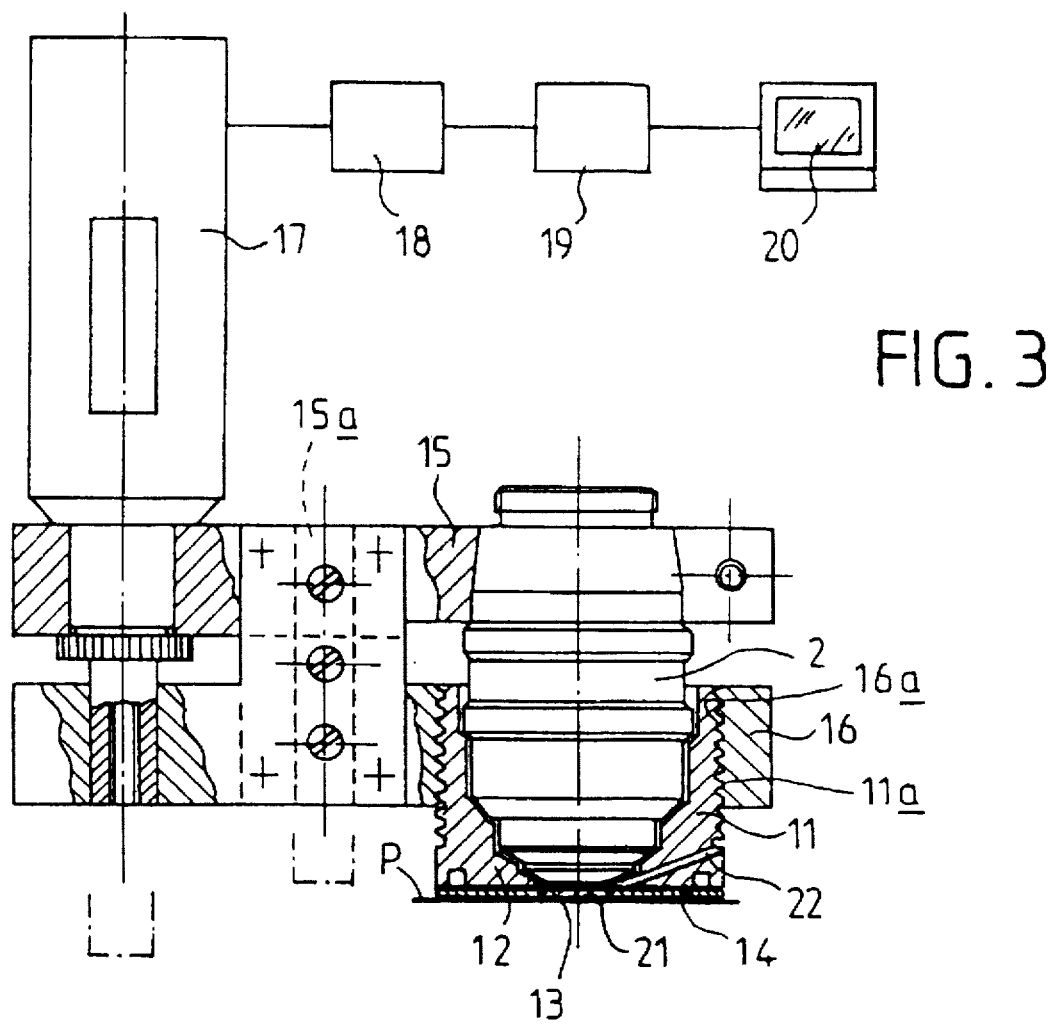
FIG. 3 is a view in elevation, with parts cut away, on a larger scale, of the lens and of the contact endpiece of the apparatus of FIG. 1.
Figure 4:
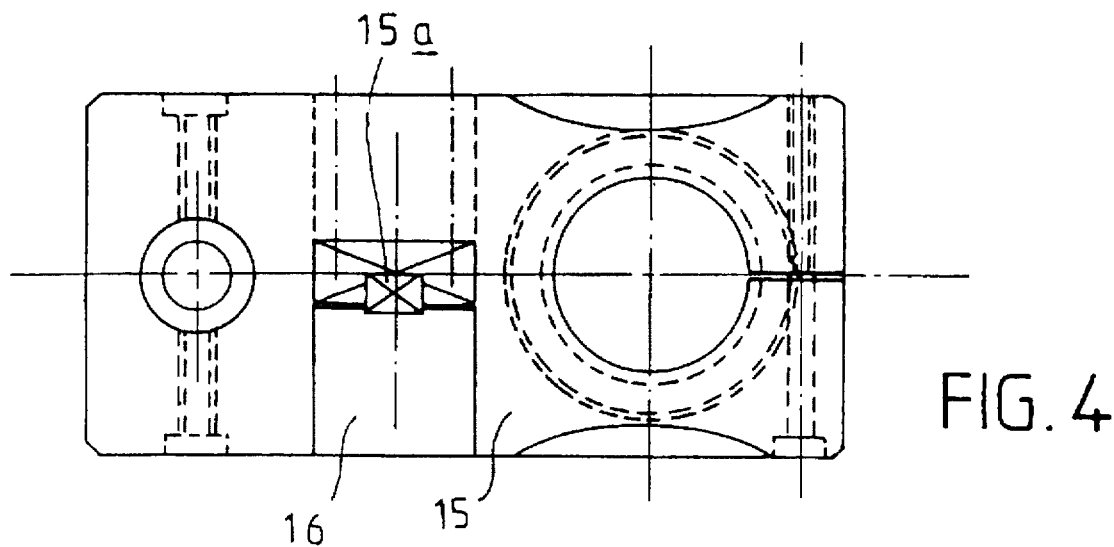
FIG. 4 is a top view in relation to FIG. 3, the lens being removed.
Figure 5:
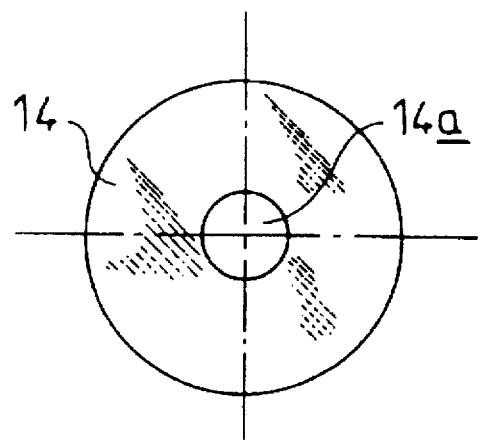
FIG. 5 is a plan view of a double-face adhesive washer.

The apparatus A includes a contact endpiece 11 which is diagrammatically represented in FIG. 1 and shown in greater detail in FIG. 3, which endpiece includes a sleeve including a base 12 provided with a circular central opening 13 having a diameter at least equal to and preferably exceeding the exit diameter of the lens 2. This lens 2, at least at its lower part, is engaged in the endpiece 11.

The contact endpiece 11 is intended to bear by the lower plane face of its base 12 against the skin P and to be linked to the skin in the annular region surrounding the opening 13.

The linkage between the endpiece 11 and the skin is advantageously realized by a double-face adhesive washer 14 which includes, in its center, a hole 14a having a diameter at least equal to that of the opening 13.

The apparatus is mounted in such a manner that a micrometric relative axial displacement is possible between the contact endpiece 11 and the lens 2.

In the embodiment of FIG. 3, the lens 2 is carried by a fixed cross member 15, which is itself carried by a frame (not shown). The contact endpiece 11 is carried by an arm 16, parallel to the cross member 15 and slidingly mounted, along a direction parallel to the axis of the lens 2, by a guidance 15a fixed on the cross member 15. The micrometric displacements of the arm 16, and thus of the contact endpiece 11, relative to the cross member 15 are provided by a precision micrometer 17, carried by the cross member 15, with a micrometer vernier.

The relative displacements between the contact endpiece 11 and the lens 2 are advantageously driven by a stepping motor 18 and a control module 19. This arrangement permits the measurement, with a precision of 1 micron, of the depths reached. Displays of the observation depths, corresponding to the relative displacements of the contact endpiece 11 and of the lens 2, can be displayed on a monitor screen 20.

The fixing of the contact endpiece 11 in the arm 16 is realized in a detachable manner by a screwing of an external threading 11a provided on the endpiece 11, into an internal threading 16a of the arm 16. It is thus possible to exchange the endpiece 11 and to choose it according to the lens and the site to be observed.

By varying the elasticity of the skin, the micrometric displacements of the contact endpiece 11 relative to the lens 2 permit the variation of the depth of the images, constituting horizontal sections of the skin, supplied by the lens 2. This depth may reach 150 microns and the possible displacements of the endpiece 11 are therefore of an amplitude at least equal to 150 microns.

A drop 21 of a liquid, the refractive index of which is substantially equal to that of the stratum corneum (the surface layer of the skin) is provided between the exit face of the lens 2 and the skin in order to suppress the interfaces and the reflections of the cutaneous surface. Advantageously, the drop 21 is a drop of immersion oil of refractive index equal to 1.5, while the refractive index of the stratum corneum is approximately 1.5.

A capillary channel 22 is provided in the endpiece 11 and opens, on the one hand, into the opening 13 and, on the other hand, on to the cylindrical peripheral surface of this endpiece 11, below the arm 16. This capillary channel 22 permits the resupply to the opening 13 of immersion oil, for example by a syringe, in order to maintain the presence of the drop 21 throughout the observation phase.

It should be noted that the adhesive washer 14 contributes to the maintenance of the meniscus of the oil drop 21.

The apparatus A includes a trough system G (see FIG. 1) to retain the member, that is to say the arm B in the example under consideration. The trough G may be articulated on pivot coupling R to permit an adjustment in a horizontal plane. The apparatus A can be displaced vertically in its entirety in order to bring the endpiece 11 into contact with the skin.

It is desirable that the apparatus according to the invention should have maximum mobility, in order to permit the relatively easy reaching of all the human body skin parts.

Figure 7:
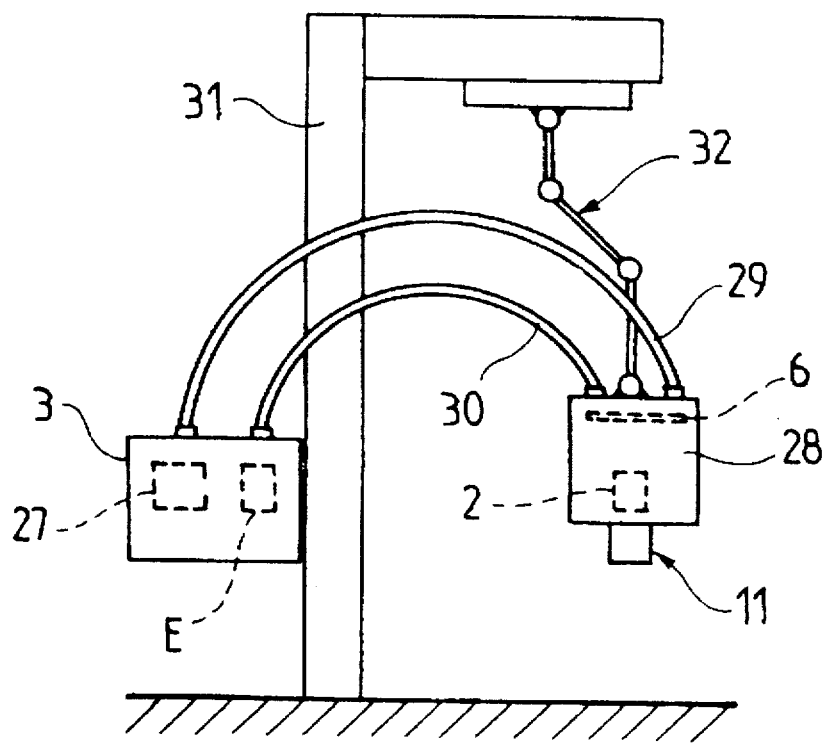
FIG. 7 is an alternate embodiment simplified diagram of a of the apparatus.

FIG. 7 of the drawings diagrammatically illustrates a modified embodiment intended to impart to the apparatus a high degree of mobility.

The light source 3 and the camera E remain fixed, in a fixed part or subassembly 27 formed for example by a casing fixed on a chassis. The other elements of the apparatus A which are shown in FIG. 1 form a movable part or subassembly 28. The optical link between the fixed part 27 and the movable part 28 is assured by two bundles 29, 30 of flexible optical fibers.

The movable part 28 is accordingly composed of the head of the microscope together with the Nipkov disk 6, the lens 2, the contact endpiece 11 and the various optical elements 4, 5, 9 and 10 appearing in FIG. 1.

The equipment formed by the movable part 28 is suspended from a fixed mast 31 via an arm 32 with pivot couplings, permitting the orientation of the movable part 28 in all directions, and its displacement to reach all the parts of the skin of the human body.

The illumination of the head of the microscope is provided by a 250 watt arc lamp, constituting the light source 3, via flexible optical fibers 29.

The image is remotely transmitted to the camera E via an image line constituted by the bundle 30 of flexible optical fibers, having a length of approximately 1 meter.

In such a variant, in the course of the observation, the contact endpiece 11 remains immovable, while micrometric displacements are communicated to the lens 2, relative to this contact endpiece 11.

In another variant, the movable equipment could include the lens 2 and the contact endpiece 11 and would thus be lighter than in the variant stated previously. The movable equipment/microscope head linkage would be assured by optical fibers after correction of the paths. In this case also, the micrometric displacements would be communicated to the lens 2 while the endpiece 11 would remain immovable in the course of the observation.

The image collected by the sensitive receiver surface 8 may undergo a processing, after recording on one band. A noise suppression may be undertaken by averaging in real time. The elimination of the bands due to the spiral arrangement of the holes 7 of the Nipkov disk 6 can be undertaken by frequency analysis.

Automatic measurements of the thicknesses of the stratum corneum and of the epidermis, by threshold processing of the epidermal nuclei, can be undertaken. In other words, by observation of the images obtained, it is possible to determine, upon the appearance of different structures, the transition from the stratum corneum to the epidermis and from the epidermis to the dermis. By referencing the amplitude of the relative displacement necessary between lens 2 and contact endpiece 11, in order to obtain these transitions, a relatively precise thickness measurement is made.

The thickness measurements may give rise to an averaging by fields in four virtual vertical cylinders having a diameter of 40 microns, the centers of which are situated on a circle and angularly offset in relation to one another by 90°, in such a manner as to correct any possible inclination of the observed surface in relation to the optical axis of the lens 2.

A volume representation with resetting of the optical sections and transparisation based on 3D+ and MIPS software may be undertaken (MISIS-St Etienne).

Figure 6:
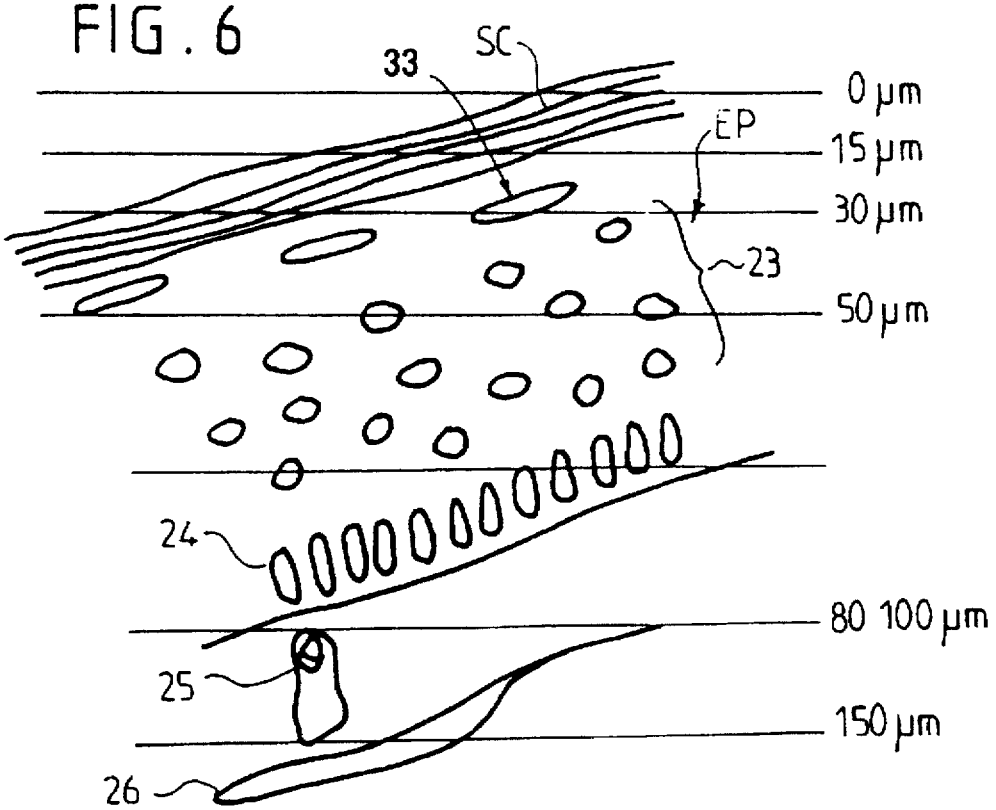
FIG. 6 is a diagrammatic cross section of the skin.

The apparatus according to the invention makes it possible to perform precise and quality observations of the skin in vivo over a depth of 150 micrometers (or microns) which reaches the capillaries, as illustrated in FIG. 6. It is thus possible to perform optical sections, in a manner which is non-invasive and non-destructive, through the stratum corneum SC, the epidermis EP (granular layer 33, spinous layer 23 and basal layer 24) and through the capillaries (terminal loops 25 and large loops 26). The average depths, expressed in micrometers, from the surface of the skin, have been indicated in FIG. 6.

The resolution is less than one micrometer and covers a field of observation having a diameter of 300 micrometers. The apparatus operates in real time; this permits operation in a 4D (three dimensions+time) space.

The contact endpiece 11 linked to the skin permits the immobilization of the field of observation while eliminating the uncontrolled movements of the patient, along two directions X, Y; this contributes to obtaining good images. The endpiece 11, fixed in a detachable manner on the arm 16, is interchangeable and its shape can be adapted to the anatomical site.

The linkage between a lower face of the base 12 of the endpiece and the skin permits the limiting of the pressure of the contact on the skin and the elimination of arterial beating. This linkage permits the maintenance of the oil meniscus and the making of precise thickness measurements.

According to the embodiment chosen, concerning the measurements of the various epidermal layers, the reproducibility of which may be affected by the movements of the patient and in particular the movements in the vertical direction, the idea was formulated of effecting the video recording of the measured zone with a rate of vertical displacement of at least 1 μm/second. For each recording, the height of the recorded layer is indicated. By virtue of a video mixing card, it is then possible to superpose the recordings of images which were made at the same depth level in the skin, thus permitting obtaining, by this superposition process, clearer images and also of a greater penetration height.

We claim:

1. An apparatus for in vivo observation of the microscopic structure of the skin, comprising:

a confocal microscope having a light source;

a rotary disk having holes therein;

a highly sensitive image receiver;

an immersion lens;

a contact endpiece, formed separate from the lens, to contact the skin and in which is received at least a lower part of the lens, wherein the contact endpiece includes a central opening and a member to adhere the contact endpiece to the skin about the central opening, wherein a liquid, a refractive index of which is substantially equal to that of the stratum corneum of the skin, is placed in the central opening of the contact endpiece between the lens and the skin, and within the member, wherein the member to adhere the contact endpiece to the skin contains the liquid therein, and wherein the contact endpiece is mounted for axial displacement relative to the lens; and a fixed subassembly including the light source and the image receiver, and a movable subassembly including a head of the microscope, the disk, the lens and the contact endpiece, wherein the contact endpiece is movable relative to the lens, and the movable subassembly is movable relative to the fixed subassembly, wherein an optical linkage between the fixed subassembly and the movable subassembly is provided by flexible optical fibers, and wherein the movable subassembly is suspended from a fixed mast via a pivotable arm.

2. An apparatus for in vivo observation of the microscopic structure of the skin, comprising:

a confocal microscope having a light source;

a rotary disk having holes therein;

a highly sensitive image receiver;

an immersion lens; and a contact endpiece, formed separate from the lens, to contact the skin and in which is received at least a lower part of the lens, wherein the contact endpiece includes a central opening and a member to adhere the contact endpiece to the skin about the central opening, wherein the contact endpiece is mounted for axial displacement relative to the lens, wherein a liquid, a refractive index of which is substantially equal to that of the stratum corneum of the skin, is placed in the central opening of the contact endpiece between the lens and the skin, and within the member, wherein the member to adhere the contact endpiece to the skin contains the liquid therein, and wherein the contact endpiece includes a capillary channel extending therethrough to the central opening of the contact endpiece, permitting a resupply of the liquid to the central opening of the contact endpiece.

3. An apparatus for in vivo observation of the microscopic structure of the skin, comprising:

a confocal microscope having a light source;

a rotary disk having holes therein;

a highly sensitive image receiver;

an immersion lens;

a contact endpiece, formed separate from the lens, to contact the skin and in which is received at least a lower part of the lens, wherein the contact endpiece includes a central opening and a member to adhere the contact endpiece to the skin about the central opening, wherein a liquid, a refractive index of which is substantially equal to that of the stratum corneum of the skin, is placed in the central opening of the contact endpiece between the lens and the skin, and within the member, wherein the member to adhere the contact endpiece contains the liquid therein, wherein the contact endpiece is mounted for axial displacement relative to the lens, and wherein the member is an adhesive washer including a central hole corresponding to the central opening of the contact endpiece; and a fixed subassembly including the light source and the image receiver, and a movable subassembly including a head of the microscope, the disk, the lens and the contact endpiece, wherein the contact endpiece is movable relative to the lens, and the fixed subassembly is movable relative to the movable subassembly, wherein an optical linkage between the fixed part and the movable part is provided by flexible optical fibers, and wherein the movable subassembly is suspended from a fixed mast via a pivotable arm.

4. An apparatus for in vivo observation of the microscopic structure of the skin, comprising:

a confocal microscope having a light source;

a rotary disk having holes therein;

a highly sensitive image receiver;

an immersion lens; and a contact endpiece, formed separate from the lens, to contact the skin and in which is received at least a lower part of the lens, wherein the contact endpiece includes a central opening and a member to adhere the contact endpiece to the skin about the central opening, wherein the contact endpiece is mounted for axial displacement relative to the lens, wherein a liquid, a refractive index of which is substantially equal to that of the stratum corneum of the skin, is placed in the central opening of the contact endpiece, between the lens and the skin, and within the member, wherein the member to adhere the contact endpiece to the skin contains the liquid therein, wherein the liquid is an immersion oil, the refractive index of which is approximately 1.5, and wherein the contact endpiece includes a capillary channel extending therethrough to the central opening of the contact endpiece, permitting a resupply of the liquid to the central opening of the contact endpiece.

5. An apparatus for in vivo observation of the microscopic structure of the skin, comprising:

a confocal microscope having a light source;

a rotary disk having holes therein;

a highly sensitive image receiver;

an immersion lens; and a contact endpiece, formed separate from the lens, to contact the skin and in which is received at least a lower part of the lens, wherein the contact endpiece includes a central opening and a member to adhere the contact endpiece to the skin about the central opening, wherein a liquid, a refractive index of which is substantially equal to that of the stratum corneum of the skin, is placed in the central opening of the contact endpiece between the lens and the skin, and within the member, wherein the member to adhere the contact endpiece to the skin contains the liquid therein, and wherein the contact endpiece is mounted for axial displacement relative to the lens.

6. The apparatus as recited in claim 5, wherein the member is an adhesive washer including a central hole corresponding to the central opening of the contact endpiece.

7. The apparatus as recited in claim 5, wherein the liquid is an immersion oil, the refractive index of which is approximately 1.5.

8. The apparatus as recited in claim 5, wherein the contact endpiece includes a capillary channel extending therethrough to the central opening of the contact endpiece, permitting a resupply of the liquid to the central opening of the contact endpiece.

* * * * *